United States Patent [19]
Fiddes et al.

[11] Patent Number: 5,837,225
[45] Date of Patent: Nov. 17, 1998

[54] TEST METHODS FOR ASSESSING K+ CHANNEL AGONIST OR MITOGENIC ACTIVITY

[75] Inventors: Ian J. Fiddes; Terence G. Kealey; Michael P. Philpott; Deborah A. Sanders; Darren M. Thompson, all of Cambridge; Gillian E. Westgate, Northampton, all of United Kingdom

[73] Assignee: Cambridge University Technical Services Ltd., Cambridge, United Kingdom

[21] Appl. No.: 628,463

[22] Filed: Apr. 5, 1996

[30] Foreign Application Priority Data

Oct. 6, 1995 [GB] United Kingdom .................. 9520411

[51] Int. Cl.⁶ .............................. A61K 7/06; C12Q 1/02; C12Q 1/04
[52] U.S. Cl. .......................... 424/70.1; 514/880; 435/29; 435/34
[58] Field of Search ................................. 424/70.1, 574; 514/880; 435/240.2, 29, 34

[56] References Cited

PUBLICATIONS

Murad et al. Supression of Fibroblast Proliferation and Lysyl Hrdroxylase Activity by Minoxidilil. Journal of Biol. Chem. 262, 11973–11978, 1987.

Dubois et al. "Role of Potassium channels in mitogenesis" Prog. Biophys. molec. Biol. vol. 59 pp. 1–21, 1993.

*Primary Examiner*—Susan A. Loring
*Attorney, Agent, or Firm*—Pillsbury Madison & Sutro LLP

[57] ABSTRACT

Method for assessing the activity of a test substance as a $K^+$ channel agonist or for mitogenic activity. Fibroblasts are cultured in a test medium which is free of aminoglycoside antibiotics, the medium is supplemented with serum or serum substitute and the test substance, and the response of the supplemented cells to the test substance is assessed.

10 Claims, 5 Drawing Sheets

FIG. 3B
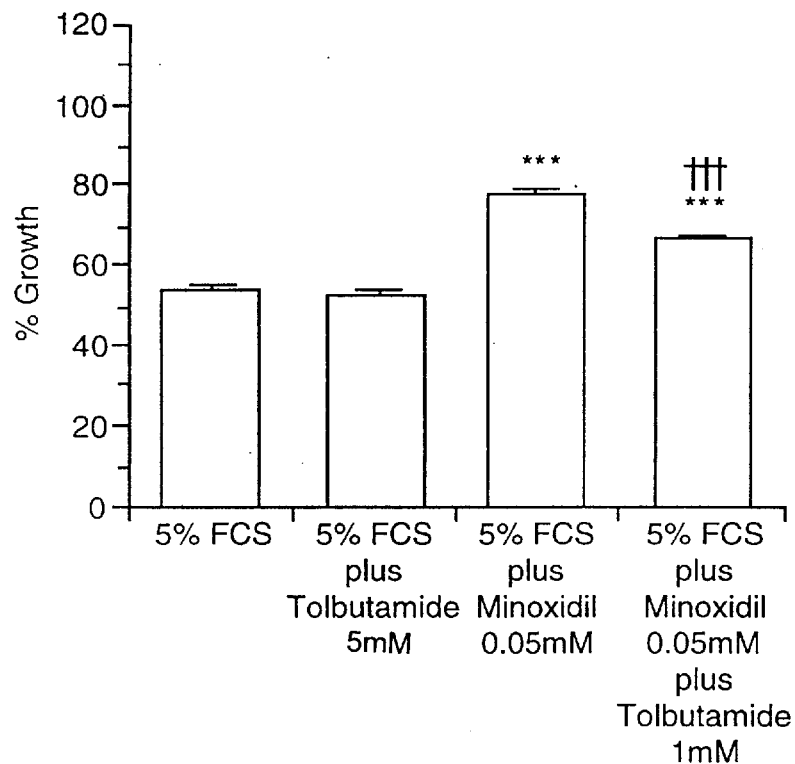
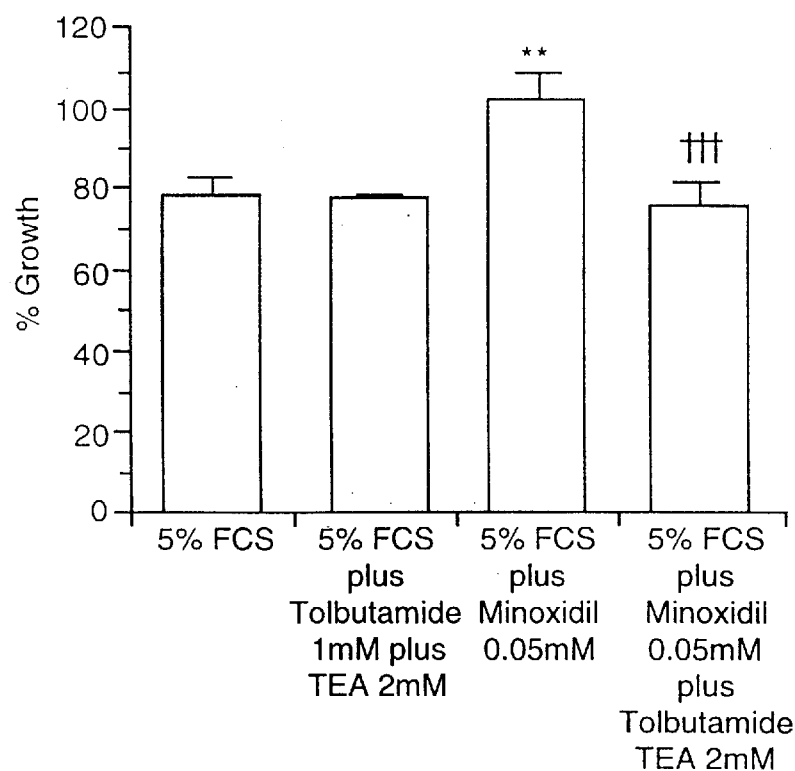
FIG. 3D

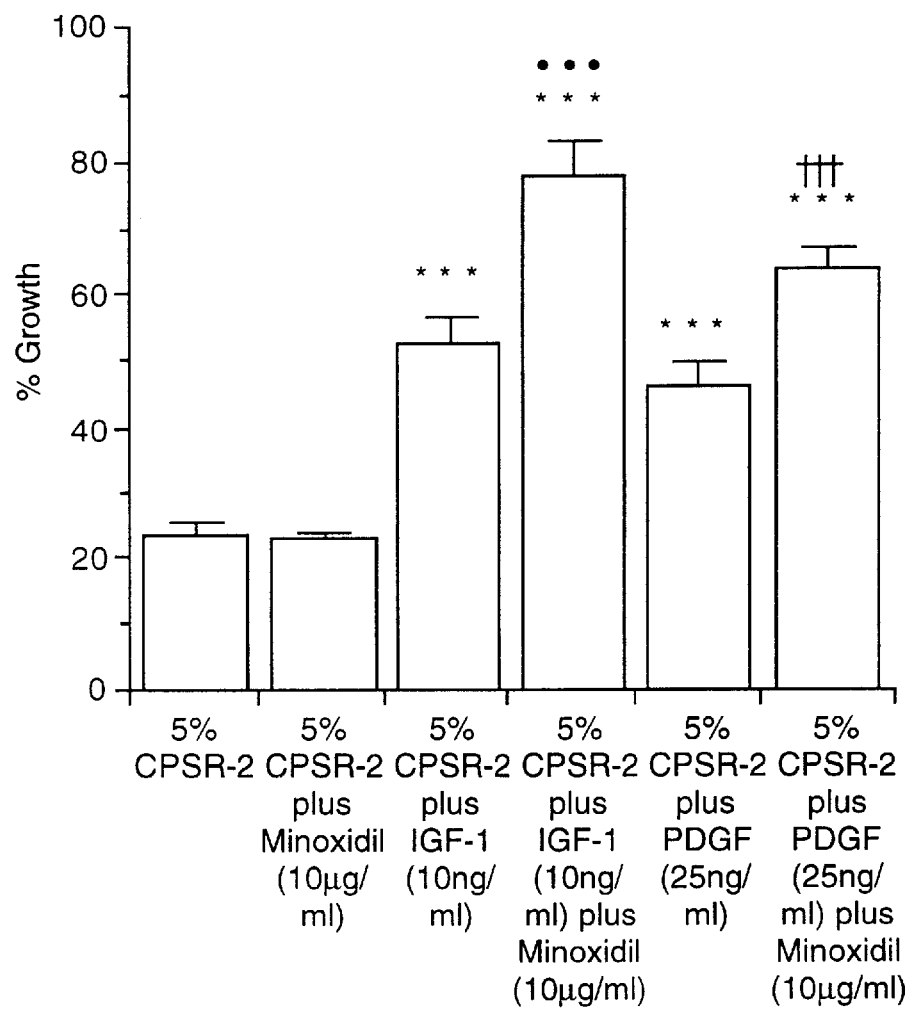

TEST METHODS FOR ASSESSING K⁺ CHANNEL AGONIST OR MITOGENIC ACTIVITY

FIELD OF THE INVENTION

The invention relates to a method of testing, in particular to a method of testing substances (such as potential hair growth actives), or compositions containing such substances, for their mitogenic ability or ability to potentiate other mitogens.

BACKGROUND

MITOGENESIS AND THE HAIR GROWTH CYCLE

The hair follicle is composed of an epithelial component, the matrix and outer root sheath enclosing the hair shaft and a dermal component, the dermal papilla within the bulb. Hair growth is effected by the division of the hair follicle basal cells and in the mammal, this is cyclical. Three distinct stages of hair growth can be identified, namely:

i. an active stage known as anagen, during which the hair follicle penetrates deep into the dermis with the cells of the bulb dividing rapidly an differentiating to form the hair, ii. a regressive stage known as catagen, which is heralded by the cessation of mitogenesis and during which the follicle regresses upwards through the dermis and hair growth ceases, and iii. a resting stage known as telogen, in which the regressed follicle contains a small secondary germ with an underlying ball of tightly packed dermal papilla cells.

The initiation of a new anagen stage is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

Loss of hair on the human head, particularly that which results in male pattern baldness, is a natural process often associated with advancing age. Baldness occurring in young people, particularly men, can give the impression that age is advancing faster than it really is.

Baldness can also result from a disorder of the skin known as Alopecia areata.

Since time immemorial, man has striven to maintain the appearance of youth with potions and lotions to preserve skin conditions and also to reverse the natural ageing process. This has applied also to hair loss, with the result that many hair restorers, hoir lotions and the like have been applied to the scalp in an attempt to slow or arrest hair loss or to increase hair growth.

Given the role mitogenesis plays in the active stage of the hair growth cycle, clearly there is a demand for substances which have mitogenic ability or the ability to potentiate mitogenesis for application in this context.

In order to determine whether any substance, such as a potential hair growth active, has mitogenic ability, or the ability to potentiate mitogen-esis, it is first necessary to carry out clinical tests involving applying the substance to the skin of a test animal, for example a rodent. Although the results of in vivo clinical tests are required to support commercial exploitation, these tests are time consuming and costly to perform.

Accordingly, there exists a need for an in vitro screening test to determine rapidly whether or not a substance, such as a potential hair growth active, at least has the potential to exhibit mitogenic ability or to potentiate mitogenesis.

THE ROLE OF K⁺ CHANNEL OPENERS IN MITOGEENESIS

There is considerable evidence to suggest that the opening of K⁺ channels plays an important role in stimulating mitogenesis. K⁺ channel blockers have been shown to inhibit mitogenesis in vitro, mitogens increase cytosolic membrane K⁺ channel permability, K⁺ channel openers stimulate hair growth in vivo and the Ras/Raf signal transduction pathway induces K⁺ channel activity.

However, in vitro attempts to demonstrate mitogenicity or its potentiation by Minoxicdil have been disappointing, with either no effect or often an inhibition of growth (Priestley et al Br J Dermatol 1991, 125, 217–221); stimulation has only been shown using very high concentrations.

We have discovered, contrary to these earlier teachings, that Minoxidil does potentiate the growth of NIH 3T3 fibroblasts (a common cell line) in vitro, but only in the absence of aminoglycoside antibiotics. whilst not wishing to be bound by any theory, it is believed that the experiments of the prior art were carried out in the presence of aminoglycoside antibiotics, and those arninoglycoside antibiotics (such as streptomycin) had an inhibiting effect on K⁺ channel activity.

We have shown that in the absence of aminoglycoside antibiotics, Minoxidil causes significant stimulation of proliferation of NIH 3T3 fibroblasts maintained in medium supplemented with foetal calf serum (FCS). Minoxidil can therefore be said to "potentiate" the mitogenic effects of the serum. We have found that this potentiation is an effect which is significant and observable so as to provide a rapid, convenient bioassay for substances thought to have an analogous mode of action to Minoxidil, namely suspected K⁺ channel agonists.

We have also found that Minoxidil potentiates, to a significant observable degree, the mnitogenic effects of the individual mitogens IGF-1 and PDGF, when fibroblasts are cultured in medium containing one of these actives in the presence of a low mitogen serum substitute instead of foetal calf serum. This is surprising, given that cell sera, such as foetal calf serum are typically very complex "cocktails" of many different mitogens, cytokines and other components. Advantageously, we now provide a rapid and convenient bioassay for individual suspected mitogens. The test now described enables the key components of complex growth media to be defined, and their effects quantified individually and precisely for the purposes of isolating suitable mitogens in the context of, for example, identification of hair growth actives. Equally, if d known individual mitogen is used, to supplement the, medium, rather than a test mitogen, the test can thus be utilised to assay instead for the presence of a K⁺ channel agonist, through the measurement of potentiation of mitogenesis observed for a test K⁺ channel agonist.

SUMMARY OF THE INVENTION

The present invention provides, in a first aspect, a test method for assessing the activity of a substance as a K⁺ channel agonist, comprising:

(i) culturing fibroblasts (or cells of an analogous, suitable cell line) in a test medium substantially free of aminoglycoside antibiotics;

(ii) supplementing the medium with (a) serum, and (b) the test substance;

(iii) assessing the response of the supplemented cells to the test substance.

In a second aspect, the present invention provides a test method for assessing the mitogenic activity of a substance comprising:

(i) culturing fibroblasts (or cells of an analogous, suitable cell line) in a test medium substantially free of aminoglycoside antibiotics;

(ii) supplementing the medium with (a) a $K^+$ channel agonist (e.g. minoxidil), (b) a low mitogen serum substitute, (c) the test substance;

(iii) assessing the response of the supplemented cells to the test substance.

In a third aspect, thief present invention provides a test method for assessing the activity of a substance as a $K^+$ channel agonist comprising:

(i) culturing fibroblasts ((or cells of an analogous, suitable cell line) in a test medium substantially free of aminoglycoside antibiotics;

(ii) supplementing the medium with (a) an individual mitogen (e.g. IGF-1 or PDGF), (b) a low mitogen serum substitute, (c) the test substance;

(iii) assessing the response of the supplemented cells to the test substance.

DETAILED DESCRIPTION

Initial Cell Culture

The procedure now to be described represents a preferred method of culture and testing and is purely illustrative of the principles set forth herein.

In a preferred method according to the first aspect of the invention, NIH 3T3 fibroblasts are initially maintained in streptomycin-free Dulbecco's modified Eagle's medium (DMEM) supplemented with 10%, FCS arid 2mM L-glutamine, in 75 cm$^2$ tissue culture flasks at 37° C. in an atmosphere of 5% $CO_2$ and 95% air.

DMEM is available from FLOF Laboratory, Rickmansworth, Herts. L-glutamine and FCS are available from Gibco, Trident House, Paisley.

Prior to testing, cells are passaged and plated out to give $10^4$ cells per well in 24 well multi-well plates. Cells are then incubated for 24 hours with DMEM supplemented with 10% FCS to aid attachment, then washed 3 times with phosphate-buffered saline (PHS).

Experimental Testing of $K^+$ Channel Agonists

The techniques described herein can be employed to test substances (such as potential hair growth promoters) or compositions containing them for their ability to act as $K^+$ channel agonists. In a preferred method according to the first aspect of the present invention, the cells cultured as described above are transferred to an experimental medium containing a level of FCS that supports sub-optimal levels of fibroblast cell growth. This is so as to maximise any observed potentiation of mitogenesis encountered. A typical level of FCS that supports a sub-optimal level of cell growth is around 5%. The test substance (e.g. 10 µg/ml Minoxidil) is then added, and cell growth/proliferation assessed, e.g. by cell counting (although the change in any physical, chemical or biochemical property of the cultured cells can be employed to assess the response of a test substance).

Experimental Testing of Mitonens

In a preferred method according to the third aspect of the invention, NIH 3T3 fibroblasts are initially cultured as described under "Initial Cell Culture" above, and then transferred to an experimental medium in which FCS is replaced with a low mitogon serurm substitute. A suitable such substitute is Controlled Process Serum Replacement-2 (CPSR-2) available from Sigrm Chemical Co., Dorset. The suitable level of low mitogen serum substitute is, similarly, around 5%. The test substance (e.g. IGF-1 at 10 ng/ml or PDGF at 25 ng/ml), and cell growth/proliferation assessed by suitable means as described above.

EXAMPLES

Materials and Methods

Materials

Tissue culture plastics were obtained from Becton Dickson, Between Towns Road, Cowley, Oxford OX4 3LY NIH 3T3 fibroblasts were obtained from the European collection of animal cell cultures, Porton Down, Salisbury, Wilts SP4 0JG. Dulbecco's modified Eagle's medium was obtained from Flow Laboratories, Rickmansworth, Herts, WD3 1PQ. L-glutamine, penicillin/streptormycin, IGF-1 and foetal calf serum were from Gibco, Trident House, PO Box 35, Renfew Road, Paisley PA3 LEF. Minoxidil was a gift from Unilever Research, Sharnbrook, Bedford. All other chemicals were obtained from Sigma Chemical Co. Ltd, Fancy Road, Poole, Dorset and were of the highest grade available.

Methods

Cell Culture

NIH 3T3 fibroblasts were Initially maintained in Dulbecco's modified Eagle's medium supplemented with 10% FCS and 2 mM L-glutarnine, in 75 cm$^2$ tissue culture flasks at 37° C. in an atmosphere of 5% $CO_2$/95% air. Antibiotics were not added unless specified. Medium was changed every three days, and passages were carried out twice a week before cells reached confluence. Prior to experiments, cells were passaged and plated out to give $10^4$ cells per well in 24 well multi-well plates. Cells were incubated for 24 hours with DMEM supplemented with 10% FCS to aid attachment, then washed 3 times with PBS and the experimental medium was added. Each experiment was carried out in triplicate.

Minoxidil

A stock solution of Minoxidil was prepared by adding 10 mg of Minoxidil to 10 mls of tissue culture medium and then gently shaking this solution at room temperature for 2–3 hours until all the Minoxidil was dissolved. This was then diluted in tissue culture medium and used at a final concentration of 10 µg/ml (0.05 m/M).

$K^+$ Channel Antaconists

Tolbutamide was made as a 410 mM stock solution in ethanol, which was then diluted in the tissue culture medium to give a final concentration of 5 mM or 1 mM. Glibenclamide was made as a stock solution of 10 mM in DMSO. This was diluted in tissue culture medium and diluted to give a final concentration of 2 mM. Apamin stock solution of 250 µM was made up in PBS and diluted in tissue culture medium to give a final concentration of 100 µM. Each experiment was carried out in triplicate. Control experiments were supplemented with either ethanol, DMSO or PBS as appropriate. Medium was changed after three days.

CPSR-2 and growth factors

Experiments were also carried out using CPSR-2, a mitogen free serum substitute to replace FCS. In some experiments medium containing CPSR-2 was additionally supplemented with either IGF-1 at 10 ng/ml or PDGF at 25 ng/ml.

Cell Counting

Tissue culture medium was removed from all wells and the cells were washed with PBS ($Ca^{2+}$ and $Mg^{2+}$ free). Cells were incubated with 0.5 mls of trypsin-EDTA per well until they became detached, then 0.5 irls of 10% FCS supplemented medium was added.

Samples were aliquoted into Eppendorf tubes and centrifuged at 6000 rpm for 5 minutes. The supernatant was removed and the cells resuspended in 100μls of PBS ($Ca^{2+}$ and $Mg^{2+}$ free) These suspensions were then counted using a hemocytometer. Results are expressed as percentage of the number of cells obtained when grown with 10% FCS.

RESULTS

The Effect of Minoxidil on Sub-Octimally Growing NIH 3T3 Fibroblasts

Experiments were carried out to identify a concentration of FCS that would support sub-optimal levels of NIH 3T3 cell growth and thus enable us to maximise any inhibition or potentiation of mitogenesis. FIG. 1 shows that, in the presence of 10% FCS, fibroblasts showed a typical growth curve and reached confluence after 10 days in culture. When fibroblasts were maintained in the presence of 5% FCS they showed a much slower rate of growth and by 7 days had produced only half the number of cells found in wells containing 10% FCS. When fibroblasts were maintained in the absence of serum there was no increase in cell numbers.

Having established that 5% FCS supported a sub-optimal level of cell growth, experiments were then carried out to study the effects of Minoxidil on NIH 3T3's in the absence and presence of streptomycin. FIG. 2 shows that when 3T3 fibroblasts were maintained in the absence of streptomycin with 10 μg/mi Minoxidil there was a significant increase in the cell numbers over the control ($p<0.001$ at day 7). However, in the presence of streptomycin cell growth was inhibited at day 4 ($p<0.01$). By day 7 there was no significant difference between the control (5% FCS) and 5% FCS plus 10 μg/ml Minoxidil. After 10 days of culture there was however a significant increase in cell numbers ($p<0.01$). The addition of Minoxidil (10 μg/ml) to cells growing in 10% FCS also produced significant stimulation of growth, giving growth 112.7%±4.4% of the control value in 10% FCS alone ($p<0.05$) after 7 days (data not shown).

This data shows that in the absence of streptomycin Minoxidil potentiates the mitogenic effects of sub-optimal levels of FCS on the growth of NIH 3T3 fibroblasts but that in the presence of streptomycin Minoxidil is initially inhibitory. This suggests that the previous reports on the inhibitory effects of Maonxidil on cell proliferation may in fact be artefactual due to the use of arninoglycoside antibiotics.

Effect of $K^+$ channel antagonists on the Minoxidil stimulated growth of NIH 3T3 Fibroblasts Having shown that, in the absence of penicillin/streptomycin, Minoxidil significantly stimulated the growth of 3T3 fibroblasts maintained under sub-optimal conditions, further experiments were carried out to determine whether the Minoxidil stimulated growth was mediated via $K^+$ channels. As the precise $K^+$ channel that Minoxidil is thought to activate is unknown at present, we looked at a number of different $K^+$ channel blockers to see if they could block the Minoxidil potentiation of the mitogenic effects of FCS on 3T3 fibroblasts.

Tolbutamide, which specifically blocks ATP-sensitive $K^+$ channels (Cook N. S. (198). TiPS.9.21–28) used at a concentration of 1 mM, caused a slight reduction in the Minoxidil-stimulated increase in cell numbers but this did not achieve statistical significance (FIG. 3A). When the concentration was increased to 5 mM (FIG. 3B) there was a significant reduction ($p<0.001$) of the Minoxidil stimulation though growth was still significantly greater than with 5% FCS alone ($p<0.01$). This therefore indicates that Minoxidil is acting as a $K^+$ channel agonist.

TEA, a weak non-selective blocker of most types of $K^+$ channels (Cook, 1988), when based at 2 mM gave a slight but not statistically significant reduction in the Minoxidil stimulation of growth (FIG. 3C). But when tolbutamide (1 mM) and TEA (2 mM) were used together, there was a significant ($p<0.01$) inhibition of Minoxidil stimulated cell growth (FIG. 3D). This, moreover, was not significantly different to that obtained in 5% FCS alone, which showed that the Minoxidil potentiation had been completely blocked. This again indicates that Minoxidil is acting as a $K^+$ channel agonist. Control experiments showed that in the absence of Minoxidil, neither tolbutamide (5 mM) nor TEA (2 mM) alone or used together had any effect on cell numbers.

Neither glibenclamide (1 μM) which blocks ATP-sensitive $K^+$ channels nor aparine (10 nM) which blocks low conductance $Ca^{2+}$-activated K+ channels (Cook, 1988) had any effect on Minoxidil stimulated cell growth when used alone (FIG. 4A and 4B respectively). When used together, however, (FIG. 4C) there was a significant inhibition of Minoxidil stimulated cell growth ($p<0.001$). Growth was not significantly different from that in 5% FCS alone, showing complete blockage of the Minoxidil potentiation.

Control experiments in the absence of Minoxidil showed that glibenclamide (1 μM) and apamin (10 nM) used together had no significant effect on cell numbers, which confirms that the tolbutamide/TEA and glibenclamide/apamin mediated inhibition of the Minoxidil potentiation of FCS mitogenesis can be attributed to their specific $K^+$ channel blocking effect rather than to non-specific cell toxicity.

Minoxidil potentiates the mitogenic effects of growth factors

To determine the Minoxidil potentiation of the mitogenesis of individual growth factors, we cultured NIH 3T3 fibroblasts in medium containing 5% CPSR-2, an essentially cytokine free FCS substitute which gave significantly lower rates of growth when compared to cells grown in medium containing 5% FCS ($p<0.001$). Moreover, when Minoxidil (10 μg/ml) was added to this medium cell growth was not stimulated (FIG. 5). However, when medium containing 5% CPSR-2 was supplemented with IGF-1(10 ng/ml) there was a marked stimulation of cell growth ($p<0.001$) and this was significantly potentiated by the addition of 10 μg/ml Minoxidil ($p<0.001$) (FIG. 5). Likewise PDGF at 25 ng/ml also stimulated cell growth over 5% CPSR-2 alone ($p<0.001$) and this was significantly stimulated by the addition of 10 μg/ml Minoxidil ($p<0.001$) (FIG. 5).

***$p<0.00$ Significance compared to growth in 5% FCS

†† $p<0.01$ Significance compared to growth in 5% FCS plus penicillin/streptomycin.

FIGS. 3A–3D. Effects of a tolbutamide and TEA on the Minoxidil stimulation of growth of 3T3 fibroblasts maintained in 5% FCS supplemented medium. (FIG. 3A) with 1 mM tolbutamide there is no significant effect on the stimulation of growth by Minoxidil. (FIG. 3B) At 5 mM tolbutamide gives a significant ($p<0.001$) reduction in the Minoxidil stimulation of growth. (FIG. 3C) TEA at 2 mM has no significant effect on the Minoxidil stimulation of growth. (FIG. 3D) Tolbutamide (1 mM) and TEA (2 mM) used together gave a significant reduction in Minoxidil stimulation ($p<0.001$). Values are expressed as a percentage of the control growth in 10% FCS after 7 days culture and shown as mean ± s.e.m. of 3 experiments performed in triplicate. Significance is shown compared to both growth in 5% FCS alone and growth in 5% FCS plus Minoxidil. In all histograms 5% PCS plus Minoxidil is significantly increased compared to 5% FCS alone ($p<0.001$ for FIGS. 3A, 3B and 3C, $p<0.01$ for FIG. 3D). Statistical significance was determined using Student's t-test.

Figure 1:
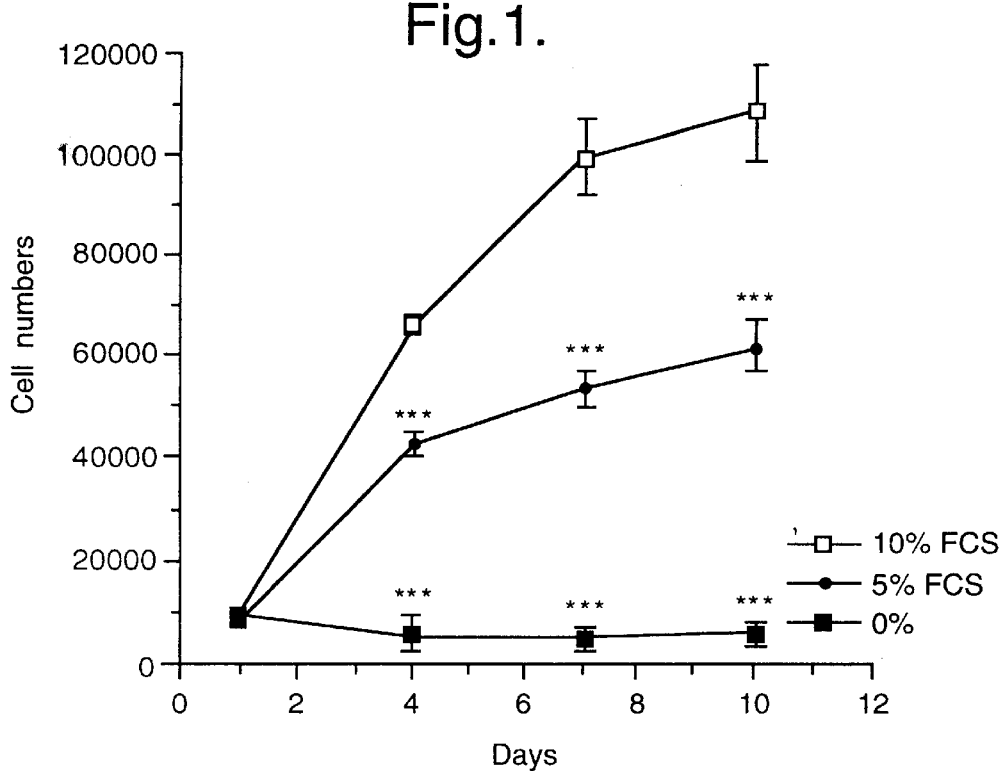
FIG. 1. Effect of serum concentration on the growth of 3T3 fibroblasts. Growth is significantly reduced with 5% FCS and in serum free conditions when compared to growth in 10% FCS. Values are expressed as cell numbers per well and are shown as mean ± s.e.m. of 3 experiments performed in triplicate. Statistical significance relative to growth in 10% FCS was determined using Student's t-test. ***$p<0.001$.
Figure 2:
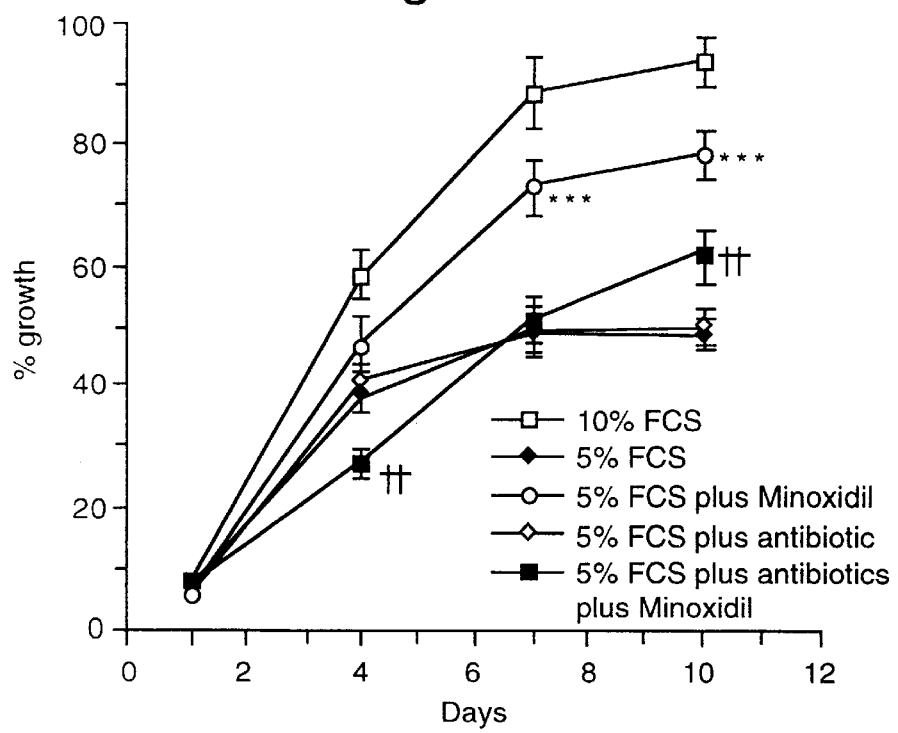
FIG. 2. Effect of Minoxidil (10 μg/ml) on the growth of 3T3 fibroblasts. In the absence of aminoglycoside antibiotics Minoxidil gives significant stimulation over growth in 5% FCS alone. In the presence of penicillin 100 U/ml and streptomycin 100 μg/ml, Minoxidil initially inhibits growth but gives slight stimulation after 10 days. Values are expressed as a percentage of the control growth in 10% FCS and are shown as mean ± s.e.m. of 5 experiments performed in triplicate. Statistical significance was determined using Student's t-test.
Figure 3A:
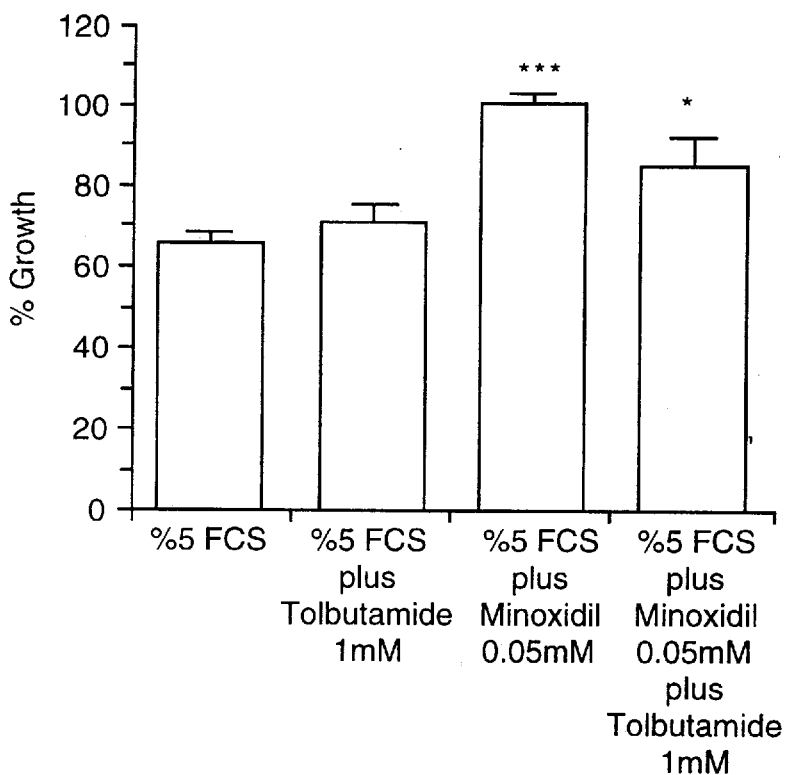
Figure 3C:
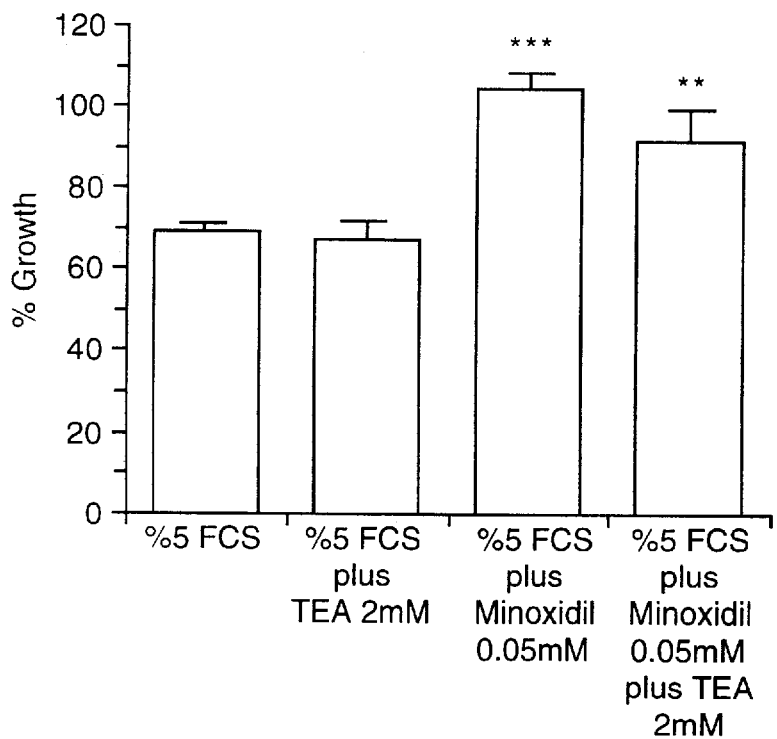
Figure 4A:
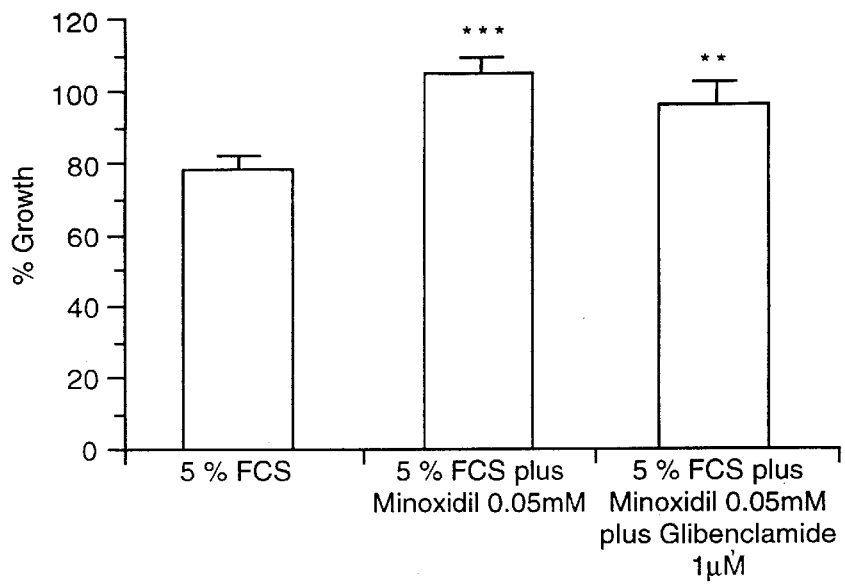
Figure 4B:
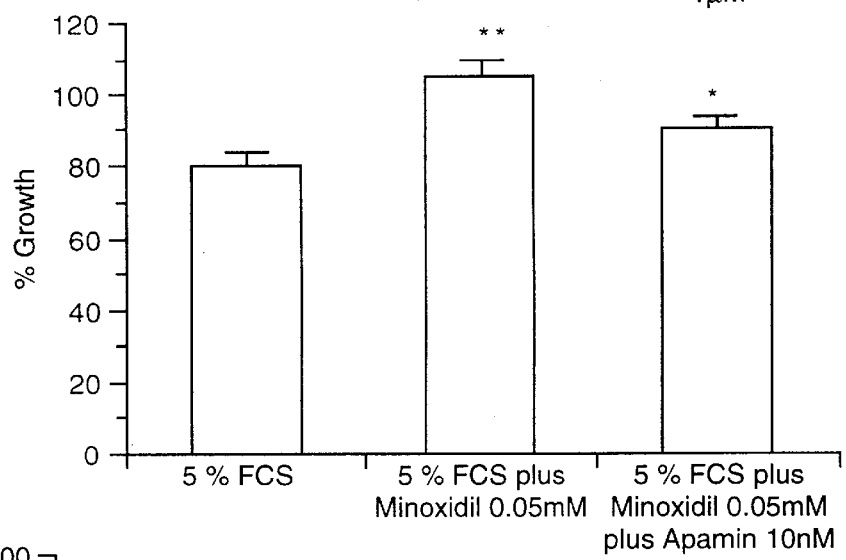
Figure 4C:
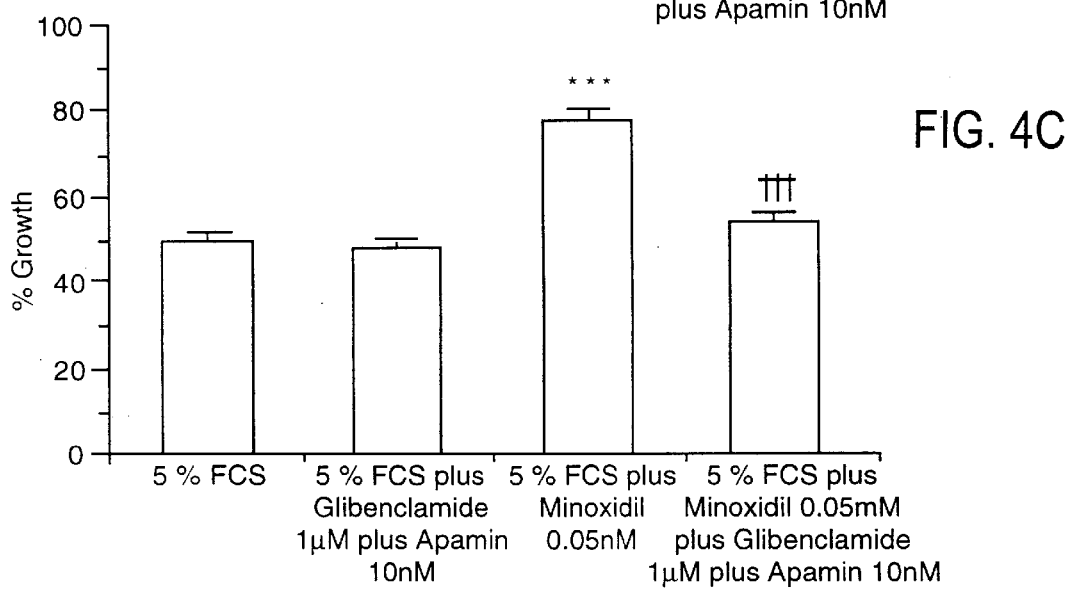

*$p<0.05$ Significance compared to growth in 5% FCS.
**$p<0.01$ Significance compared to growth in 5% FCS.
***$p<0.001$ Significance compared to growth in 5% FCS.
††† $p<0.001$ Significance compared to growth in 5% FCS plus Minoxidil FIGS. 4A, 4B and 4C. Effects of glibenclamide and apamin on the Minoxidil stimulation of NIH 3T3 fibroblasts maintained in 5% FCS supplemented medium. (FIG. 4A) with 1 μM glibenclamide there is no significant effect on the stimulation of growth by Minoxidil. (FIG. 4B) Apamin at 10 nM also has no significant effect on the Minoxidil stimulation. (FIG. 4C) Glibenclamide (1 μM) and apamin (10 nM) used together significantly reduced the Minoxidil stimulation ($p<0.001$). Values are expressed as a percentage of the control growth in 10% FCS after 7 days culture and shown as mean ± s.e.m 3 experiments performed in triplicate. Significance is shown compared to both growth in 5% FCS alone and growth in 5% FCS plus Minoxidil.

In all histograms 5% FCS plus Minoxidil is significantly increased compared to 5% FCS alone ($p<0.001$ for FIG. 4A and FIG. 4C, $p<0.01$ for FIG. 4B). Statistical significance was determined using Student's t-test.

*$p<0.05$ Significance compared to growth in 5% FCS.
**$p<0.01$ Significance compared to growth in 5% FCS.
***$p<0.001$ Significance compared to growth in 5% FCS.
†††$p<0.001$ Significance compared to growth in 5% FCS plus Minoxidil.

FIG. 5. Effects of Minoxidil, EGF-1 and PDGF on the growth of NIH 3T3 fibroblasts maintained in 5% CPSR-2. Values are expressed as a percentage of the control growth in 10% FCS after 7 days culture. Minoxidil has no effect in 5% CPSR-2 alone. Addition of IGF-1 (10 ng/ml) or PDGF (25 ng/ml) gives significant stimulation over growth in 5% CPSR-2 alone ($p<0.001$). Minoxidil gives significant stimulation when added with IGF-1 or PDGF, over growth with the cytokine alone ($p<0.001$).

***$p<0.001$ Significance compared to growth in 5% CPSR-2.

... $p<0.001$ Significance compared to growth in 5% CPSR-2 plus IGF-1.

†††$p<0.001$ Significance compared to growth in 5% CPSR-2 plus PDGF.

We claim:

1. A test method for assessing the activity of a test substance as a $K^+$ channel agonist, comprising:
   (i) culturing fibroblasts in a test medium free of aminoglycoside antibiotics;
   (ii) supplementing the medium with (a) serum, and (b) the test substance;
   (iii) assessing the response of the supplemented cells to the test substance as a basis for determining $K^+$ channel agonist activity.

2. A test method according to claim 1 in which the serum is foetal calf serum.

3. A test method according to claim 2 in which the level of foetal calf serum in the medium is about 5%.

4. A test method for assessing the mitogenic activity of a substance test comprising:
   (i) culturing fibroblasts in a test medium free of aminoglycoside antibiotics;
   (ii) supplementing the medium with (a) a $K^+$ channel agonist, (b) a cytokine-free serum substitute, (c) the test substance;
   (iii) assessing the response of the supplemented cells to the test substance.

5. A test method for assessing the activity of a substance as a $K^+$ channel agonist, comprising:
   (i) culturing fibroblasts in a test medium free of aminoglycoside antibiotics;
   (ii) supplementing the medium with (a) known individual mitogen, (b) a low mitogen serum substitute, (c) the test substance;
   (iii) assessing the response of the supplemented cells to the test substance as a basis for determining $K^+$ channel agonist activity.

6. A test method according to claim 4 or claim 5, in which the low mitogen serum substitute is Controlled Process Serum Replacement-2.

7. A test method according to claim 6, in which the level of Controlled Process Serum Replacement-2 in the medium is about 5%.

8. A test method according to claim 4 in which the $K^+$ channel agonist is Minoxidil.

9. A test method according to claim 5 in which the known individual mitogen is IGF-1 or PDGF.

10. A test method according to claim 1, 4 or 5 in which the fibroblasts are NIH-3T3 fibroblasts.

* * * * *